United States Patent

Webb et al.

[11] Patent Number: 6,099,125
[45] Date of Patent: Aug. 8, 2000

[54] COAXIAL SPATIALLY RESOLVED REFRACTOMETER

[75] Inventors: Robert H. Webb, Lincoln; Stephen A. Burns, Reading, both of Mass.; Carl Murray Penney, Saratoga Springs, N.Y.

[73] Assignee: Schepens Eye Research Foundation, Boston, Mass.

[21] Appl. No.: 09/206,464

[22] Filed: Dec. 7, 1998

[51] Int. Cl.[7] ....................................................... A61B 3/10
[52] U.S. Cl. ............................................................ 351/211
[58] Field of Search ................................... 351/205, 206, 351/207, 208, 211, 212, 210, 214, 215, 221; 356/128, 131, 132; 600/473, 476

[56] References Cited

U.S. PATENT DOCUMENTS

| | | | |
|---|---|---|---|
| 4,609,287 | 9/1986 | Kohayakawa | 356/124 |
| 4,772,120 | 9/1988 | Pointeau | 356/124.5 |
| 5,258,791 | 11/1993 | Penney et al. | 351/211 |
| 5,757,463 | 5/1998 | Kohayakawa | 351/214 |
| 5,847,805 | 12/1998 | Kohayakawa et al. | 351/210 |

*Primary Examiner*—George Manuel
*Attorney, Agent, or Firm*—W. Hugo Liepmann; Foley, Hoag & Eliot, LLP

[57] ABSTRACT

A refractometer provides a reference path coaxial with a measurement path and thereby simplifies construction by reducing the number of parts and simplifies maintenance by halving the number of optical axes to be aligned. The refractometer includes a reference projector for projecting a reference pattern on a reference pattern position on a detector during a reference interval, a site-selector for selecting a measurement site on an optical system, and a measurement projector for projecting a measurement pattern through this selected measurement site and onto a measurement pattern position on the detector during a measurement interval. The reference projector, the site selector, and the measurement projector are all aligned along the same optical axis. In the case in which the optical system is a human eye, the designated site in typically a site on the cornea and the detector is the retina of the eye. The refractometer provides an aligner for aligning the reference pattern position with a measurement pattern position. The amount by which these two positions are moved in order to achieve alignment provides a measure of the optimal wavefront corresponding to the measurement site.

66 Claims, 12 Drawing Sheets

COAXIAL SPATIALLY RESOLVED REFRACTOMETER

This invention relates to the field of instrumentation for optical measurements and, in particular, to instruments for determining the direction of the vector normal to the optimal wavefront at selected points of an optical system. An optimal wavefront of an optical system is that wavefront which is brought to an optimal focus by the optical system. In the case of an ideal optical system, the optimal wavefront is a planar wavefront.

BACKGROUND

The action of an optical system can be considered as a transformation that operates on an incident wavefront to generate a transmitted wavefront. In many optical systems, different points on the wavefront experience different transformations depending on what portions of the optical system they traverse. For example, when a wave is incident on a lens, those portions of the wavefront that traverse the periphery of the lens will experience phase delays which differ from those experienced by those portions of the wavefront that illuminate the center of the lens. Since a wavefront is a locus of points having constant phase, this results in a transmitted wavefront having a shape that differs from that of the incident wavefront. By appropriately shaping and positioning lenses, one can conform the shape of the output wavefront of an optical system to a desired shape.

In some cases, an optical system is known to produce an incorrect transformation and the optical designer's role is to design a second optical system to correct that deficiency. For example, in the case of a human eye requiring a corrective lens, the optical components of the human eye perform an optical transformation that is imperfect. In another example, one might inadvertently install a flawed objective lens in a large telescope. Rather than attempting to replace the objective lens, it may be preferable to install a corrective lens. In both of these cases, it is useful for the designer of corrective lenses to know the nature of the flawed optical transformation.

An optical transformation can be pictured as the change in the shape of the wavefront illustrated in FIGS. 12A–12C, which illustrate physical principles underlying optical transformations. FIG. 12A shows a known optical system in which an incident plane wave is transformed into a spherical wave. The system in FIG. 12A is therefore representative of a human eye which does not require corrective lenses.

FIG. 12B shows a known optical system representative of a human eye in need of correction. In contrast to the system of FIG. 12A, this system shows a planar wavefront transformed into an irregular wavefront. The eye's inability to bring this irregular wavefront into focus on the retina causes the perceived image to appear distorted or blurred.

FIG. 12C shows the optical system of FIG. 12B but with an "optimal wavefront" incident on the system. The shape of this optimal wavefront is chosen such that the transformation provided by the optical system in FIG. 12B results in a spherical wavefront instead of the irregularly shaped wavefront shown in FIG. 12B. It is apparent from comparison of FIGS. 12A and 12C that a corrective optical system which transforms an incident wavefront into this optimal wavefront before the wave undergoes the flawed optical transformation has the effect of correcting for the flawed optical transformation.

Once the wavefront normal vectors at selected points on the wavefront are known, one can estimate the shape of the wavefront. Using this estimate of the wavefront shape, one can then design an optical system that corrects for the flawed optical transformation.

A common method for measuring the optical characteristics of a human eye is a simple substitution technique of placing lenses having different correction factors in front of the eye and asking the patient whether or not the overall image has improved. Using this method, a clinician can determine an overall correction for the optical characteristics of the eye. The instrument that is typically used to approximate an optical system that corrects for the flawed optical transformation of an eye is referred to as a "refractometer." In the case of a general lens system, corrections are determined by a variety of tests, each referred to by its own name, such as the "Foucault test." Throughout this specification, the term "refractometer" will be used to refer to instruments that make such tests.

The simple substitution technique determines the overall correction for the eye, but it is limited to prismatic, cylindrical, and spherical corrections. These corrections provide only the lower-order terms of the Siedel or polynomial model of the eye's optical system. The foregoing method does not correct for the errors that are specified by higher-order terms of the Siedel or polynomial model. Additionally, it is not possible, using this method, to obtain point-by-point measurements of the optimal wavefront's normal vector at designated sites on an optical system having spatial extent. For example, where the optical system is a cornea, it is not possible, using this method, to determine the optimal wavefront's normal vector at each point on the cornea.

A number of refractometers have been developed that are designed to determine the optimal wavefront at designated sites on an optical system. For example, Penney et al. U.S. Pat. No. 5,258,791, incorporated herein by this reference, describes an optical system including (i) a reference optical subsystem for projecting a reference pattern on the patient's retina through a reference area on the cornea, and (ii) a separate measurement optical subsystem for projecting a measurement pattern on the patient's retina through a measurement area on the cornea.

To determine the shape of the optimal wavefront at a designated site on the cornea using the refractometer disclosed in Penney, the measurement pattern is moved across the retina until its location coincides with the location of the reference pattern. Based on the difference between the initial and final positions of the measurement pattern, the refractometer disclosed in Penney can infer the direction of the vector normal to the optimal wavefront at the selected corneal site.

A disadvantage of the device disclosed in Penney is, simply put, that it has far too many parts. As a result, it is costly to acquire, complex to assemble, and requires frequent alignment during operation. What is therefore desirable in the art is a refractometer that provides the functionality of the Penney refractometer at reduced cost and complexity and without the need for frequent alignment.

SUMMARY

A refractometer according to the invention provides a reference path that is coaxial with a measurement path. This feature of the invention simplifies construction by reducing the number of parts and simplifies maintenance by halving the number of optical axes to be aligned.

In a refractometer embodying the invention, two spatial light pattern generators are aligned along a common optical axis. The term "spatial light pattern generator" is used throughout this specification to refer to any device that changes a property of light, such as brightness, according to a spatially variable pattern. As used herein, spatial light pattern generators include holes in an opaque masking material, electronically addressable transmissive or reflective arrays, and light sources having controllable brightness patterns.

The first spatial light pattern generator of the refractometer is optically conjugate to a measurement plane at which the optimal wavefront's normal vector is to be determined. This measurement plane is coplanar with a pupil of the lens system, a pupil or cornea of an eye, or a similar structure whose optical properties are of interest. The second spatial light pattern generator is optically conjugate to a detector plane on which a detector spatially responsive to a light source can be placed. Three non-limiting examples of such a detector are a CCD array, a quadrant detector, or the retina of an eye. In optical design terminology, a plane often refers to the apical position of a surface. It is in this sense that the term "plane" is used throughout this specification.

A controller coupled to the first and second spatial light pattern generators operates the refractometer in two time intervals: a measurement interval, and a reference interval. During the measurement interval, the measurement pattern is projected through a selected measurement site on the measurement plane, and, ultimately, to a measurement pattern position on the detector plane. During the reference interval, a reference pattern is projected through a generally different site, referred to as the "selected reference site," on the measurement plane and onto a generally different reference pattern position on the detector plane. The controller switches between operating the refractometer in the reference interval and operating it in the measurement interval rapidly enough so that, as a result of persistence of vision, the measurement pattern and the reference pattern appear, to a detector or a human observer, to be projected simultaneously. Alternatively, the measurement interval and the reference interval can temporally overlap or, in the limit, can be contemporaneous.

The refractometer of the invention includes an image aligner for controlling the location of the measurement pattern during the measurement interval. By operation of the aligner, the measurement pattern can be moved relative to the reference pattern. The distance and direction that the measurement pattern is moved in order to align it with the reference pattern on the detector plane provides a measure of the normal vector of the optimal wavefront at the measurement plane.

The refractometer can further include lenses that make the detector plane optically conjugate to a reference plane, at which the reference pattern is generated, and to an object plane, at which the measurement pattern is generated. Other, or the same, lenses in the refractometer can make the measurement plane optically conjugate to a site-selection plane, at which the sites or areas on the measurement plane used during the reference and the measurement intervals are selected.

A refractometer embodying this invention consists of two optical subsystems aligned along substantially the same optical axis: a reference optical subsystem and a measurement optical subsystem. The reference optical subsystem projects a reference pattern onto a reference pattern position on a detector plane through a selected reference site on the measurement plane. The measurement optical subsystem projects a measurement pattern onto a measurement pattern position on the detector plane through a selected measurement site on the measurement plane. These two subsystems can have some elements in common. The fact that the two subsystems are aligned along the same optical axis is a distinguishing feature of this invention. A second distinguishing feature of this invention is that the subsystems may be temporally rather than spatially distinct. In the case in which the optical system to be evaluated is a human eye, the measurement plane can be at the cornea or pupil of the eye being evaluated and the detector can be the retina of that eye.

In one preferred embodiment, the location of the measurement pattern on the detector can be controlled by an observer through the use of an optical aligner coupled to the measurement optical subsystem. Using this optical aligner, the observer can move the measurement pattern on the detector until it is aligned with the reference pattern on the detector. The distance and the direction in which the observer moves the measurement pattern in order to align it with the reference pattern provide a measure of the shape of the optimal wavefront associated with the portion of the wave incident on the selected measurement site on the measurement plane. In the case in which the optical system is the human eye, the observer is typically the patient. However, the observer can also be an automatic computer processor that is coupled to a detector that observes the retina and that can determine the relative locations of the reference pattern and of the measurement pattern on the retina.

In embodiments of the invention disclosed herein, a first spatial light pattern generator functions as a moveable aperture and a second spatial light pattern generator functions as a moveable light source. In a first embodiment, the moveable aperture is conjugate to the measurement plane and the moveable light source is conjugate to the detector plane. A second embodiment reverses this. In the second embodiment, it is the moveable aperture that is conjugate to the detector plane and the moveable light source that is conjugate to the measurement plane.

A reference optical subsystem for practice of the invention can include a spatial light pattern generator located at a reference plane conjugate to the detector plane and a light source for illuminating that spatial light pattern generator. Where the optical system is the eye, the detector is a retina and the reference plane is a proximal retinal conjugate plane. In the first embodiment, the reference optical subsystem can include a clear plate on which is engraved a reticle and a light source for illuminating the reticle. In this first embodiment, the measurement interval and the reference interval can be contemporaneous. In the second embodiment, the first spatial light pattern generator generates both reference and measurement light patterns in alternating time intervals, and the second spatial light pattern generator selects both the reference and measurement sites in the corresponding time intervals.

In the first embodiment, the site-selecting spatial light pattern generator provides a small aperture mask or light source that can be moved, under the control of a processor such as a computer, to selected positions in a site-selection plane. This site-selection plane is optically conjugate to a measurement plane on which is disposed the optical system whose optimal wavefront is sought. Where the optical system is the eye, the measurement plane is coplanar with the cornea or pupil. Where the optical system is a non-living lens system, the measurement plane can be coplanar with the pupil of the lens system.

Because the site-selection plane and the measurement plane are conjugates of one another, all light emanating from a selected point on the site-selection plane is directed to a corresponding point on the measurement plane. Since each point on the site-selection plane corresponds to a point on the measurement plane, when the site selector moves the mask or light source to a particular location on the site-selection plane, it also selects a measurement site on the measurement plane. This has the effect of selecting a measurement site on the cornea or pupil of the eye, or on the pupillary plane of the lens system.

In the first embodiment, the site selector can be implemented as a moveable aperture on the site-selection plane operating in conjunction with a light source behind the aperture. In the second embodiment, the site selector can be implemented as a small, moveable light source on the site-selection plane.

The optical measurement subsystem for either illustrated embodiment of the invention includes a light source or mask at an object plane optically conjugate to the detector plane. Where the optical system is the eye, the object plane can be optically conjugate to the retina of the eye. Where the optical system is a lens system, the object plane can be optically conjugate to a detector at the lens system's image plane. In the second embodiment, the light source can be formed by addressing selected light modulating elements in a spatial light pattern generator on the object plane in a manner that forms a small aperture through which light from a light source can pass. In the first embodiment, the light source can be formed directly by providing a spatial light pattern generator and by either addressing selected areas of the spatial light pattern generator.

Where the optical system to be evaluated is a system of lenses, the refractometer is as described above but with the retinal conjugate plane replaced by a plane conjugate to a detector and with the corneal conjugate plane replaced by a plane which is optically conjugate to the plane at which optical correction is to be effected. The detector in such a case can be an array responsive to the spatial location of an optical pattern, such as a CCD array or quadrant detector.

The foregoing and other objects, features and advantages of the invention will be apparent from the following description and from the accompanying drawings.

DESCRIPTION OF ILLUSTRATED EMBODIMENTS

Figure 1:
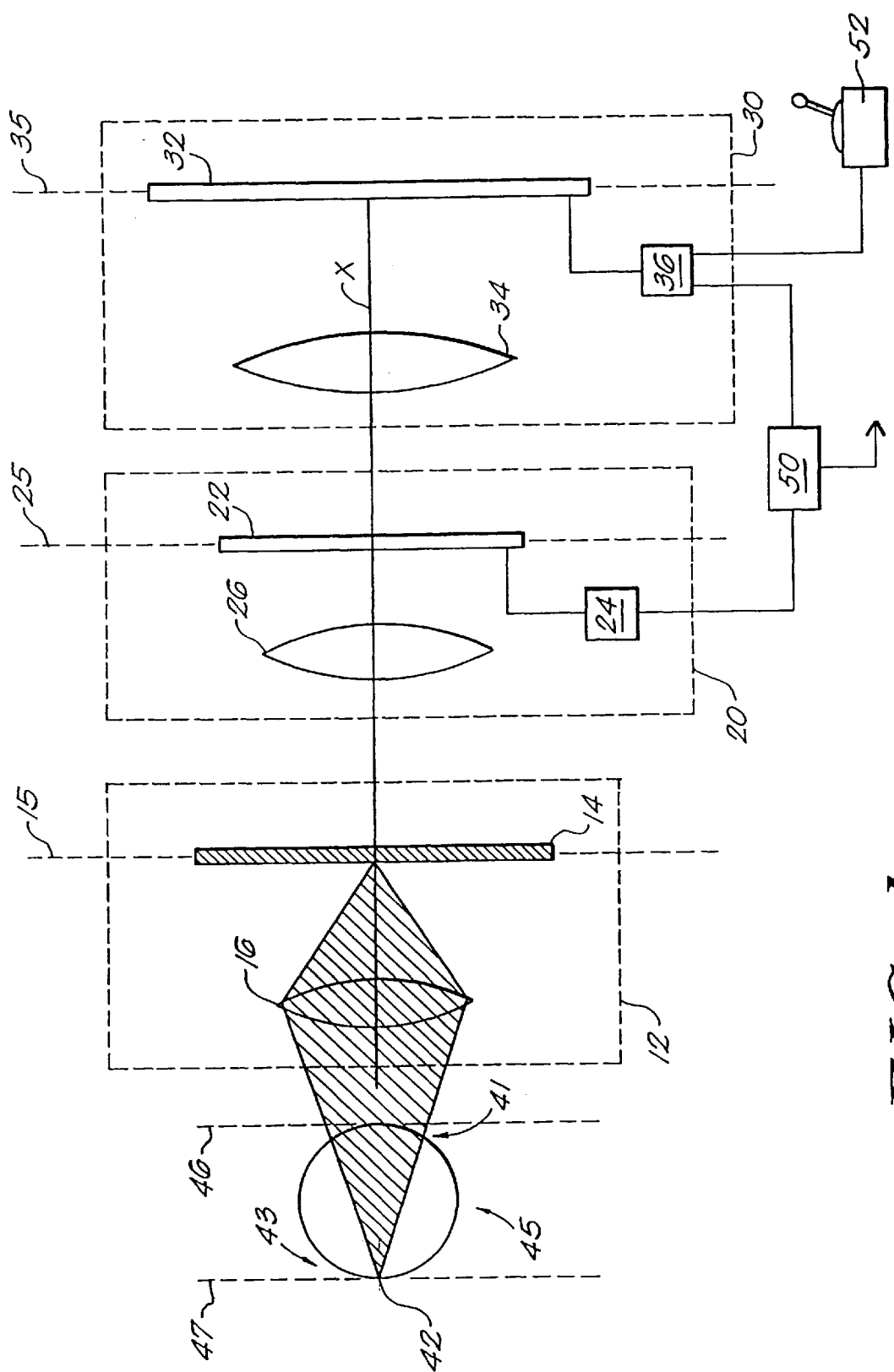
FIG. 1 shows a refractometer projecting a reference pattern on the retina of an eye in a first embodiment of the invention.
Figure 2:
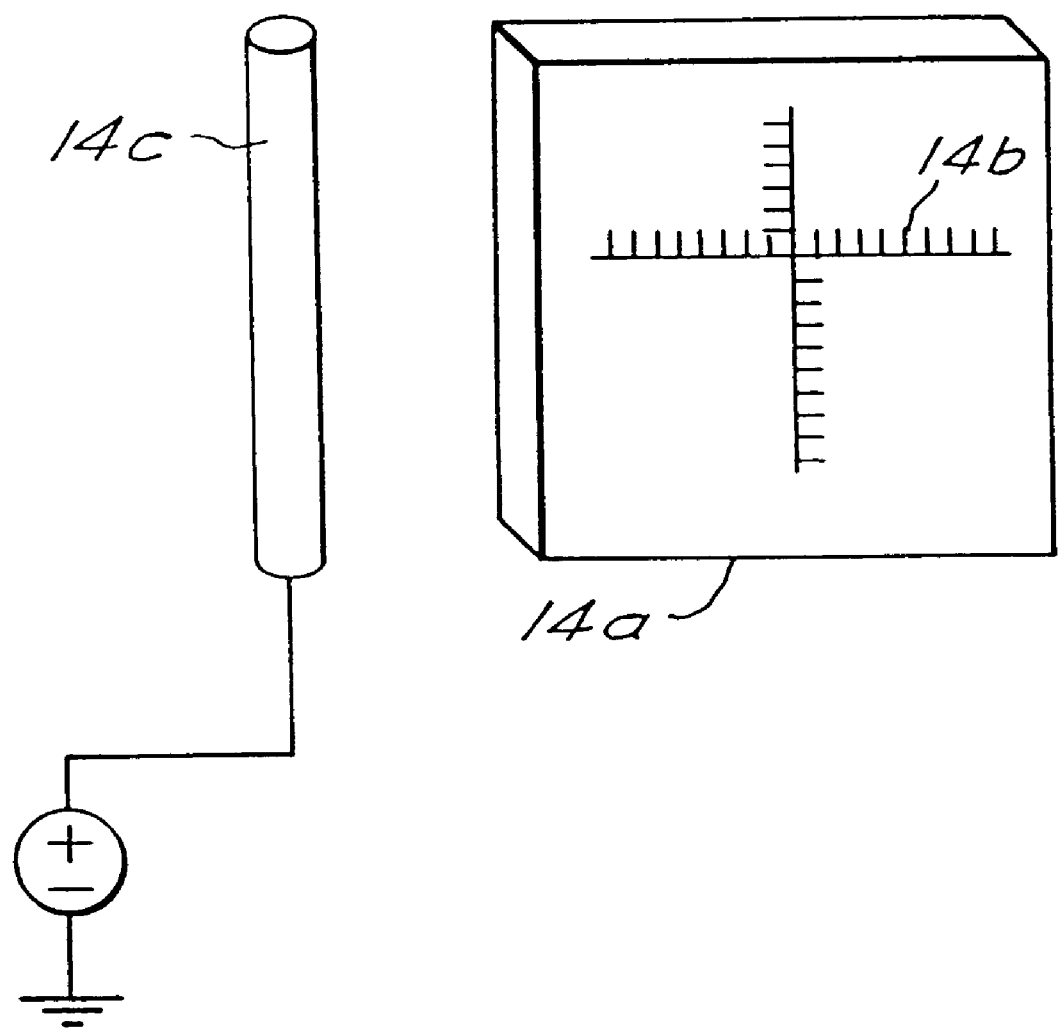
FIG. 2 is a perspective view of an illuminated reticle for projecting the reference pattern in FIG. 1.
Figure 3:
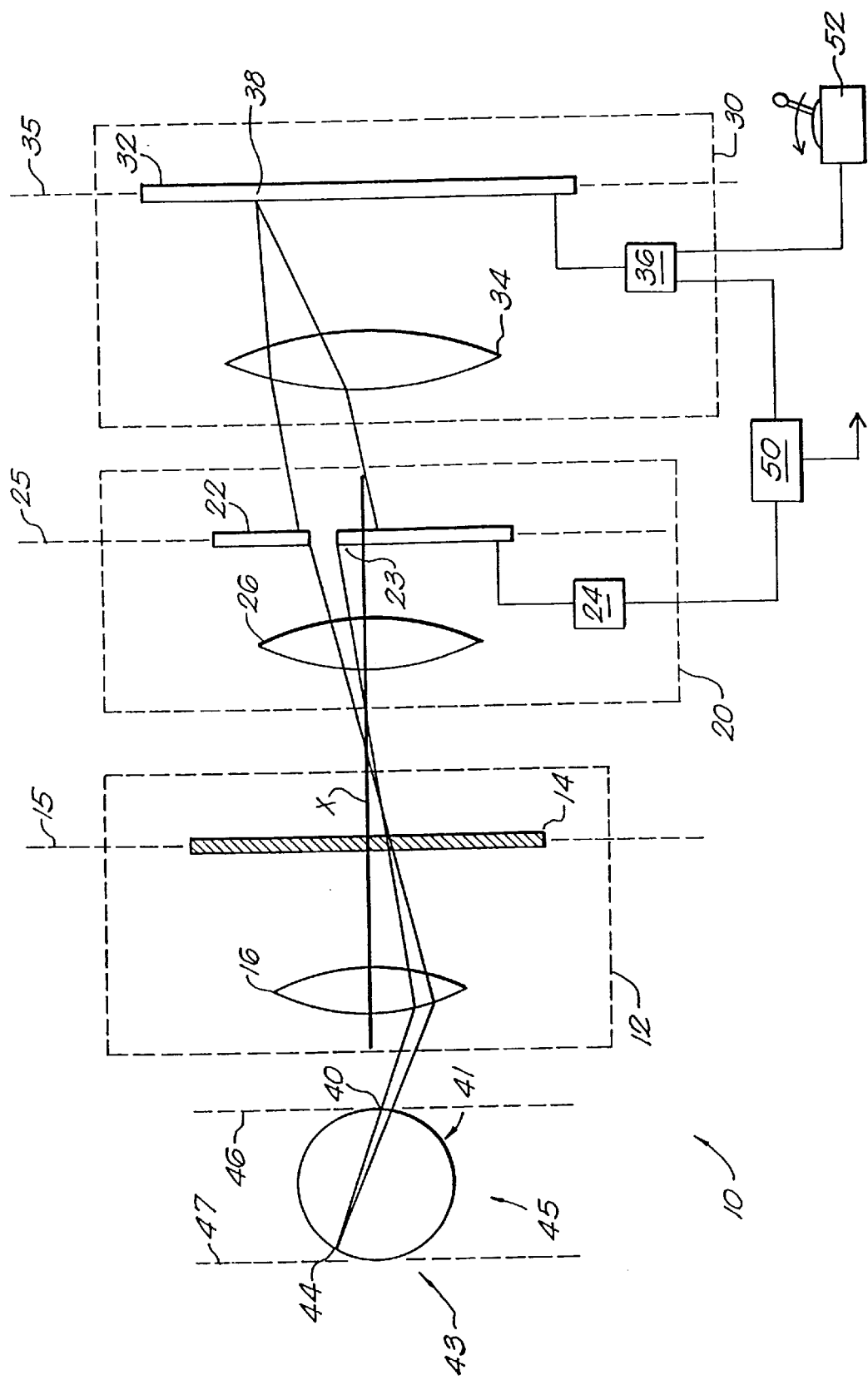
FIG. 3 shows a measurement pattern being projected on the retina of the eye in the embodiment depicted in FIG. 1.

In one embodiment, shown in FIGS. 1 and 3, a refractometer 10 according to the invention includes an illuminated reticle 14 coplanar with a reference plane 15 which is optically conjugate to a detector plane 47. A first lens 16 is disposed along the optical axis X between the illuminated reticle 14 and a measurement plane 46. The illuminated reticle 14, shown in more detail in FIG. 2, is typically a transparent plate 14a having a cross or other reference mark 14b etched on the plate. The transparent plate 14a is illuminated by a light source 14c adjacent to the plate. Together, the illuminated reticle 14 and the lens 16 form a reference optical subsystem 12.

The refractometer 10 further includes a mask 22 coplanar with a site-selection plane 25 optically conjugate to the measurement plane 46. The mask 22 has a moveable site-selecting aperture 23 (FIG. 3) whose location in the site-selection plane 25 is controlled by an aperture controller 24 connected to a processor 50. A second lens 26 is disposed along the optical axis X between the mask 22 and the illuminated reticle 14. Together, the mask 22 and the lens 26 form a site designator 20 for selecting a measurement site 40 on the measurement plane 46.

When the refractometer 10 measures the optical properties of an eye 45, as shown in FIGS. 1 and 3, the eye 45 is positioned between the measurement plane 46 and the detector plane 47 with the retina 43 of the eye 45 being approximately coplanar with the detector plane 47 and with the cornea 41 of the eye 45 being approximately coplanar with the measurement pane 46.

Figure 6A:
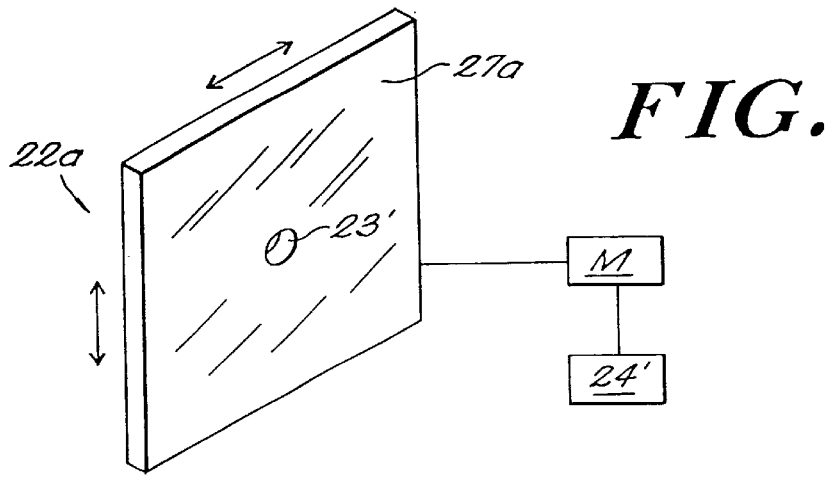
FIG. 6A shows the mask of FIGS. 1 and 3 implemented with an opaque screen and a stepping motor.

The mask 22 of the refractometer 10 in FIG. 1 can be implemented in a variety of ways. These include the mechanically actuated mask 22a shown in FIG. 6A and the electronically actuated mask 22b shown in FIG. 6B. As shown in FIG. 6A, one illustrated mask 22a for use with the refractometer 10 of FIG. 1 and having a moveable site-selecting aperture 23' is implemented by coupling a stepping motor M to both an aperture controller 24' and an opaque screen 27a having an aperture 23'. The aperture controller 24' in this embodiment is a processor which receives a signal representative of the desired location for the aperture 23' from the processor 50 and translates the desired location into signals which control the action of the stepping motor M. In response to signals from the aperture controller 24', the stepping motor M translates the opaque screen 27a in the site-selection plane 25, thereby translating the aperture 23' in the site-selection plane 25 as well.

Figure 6B:
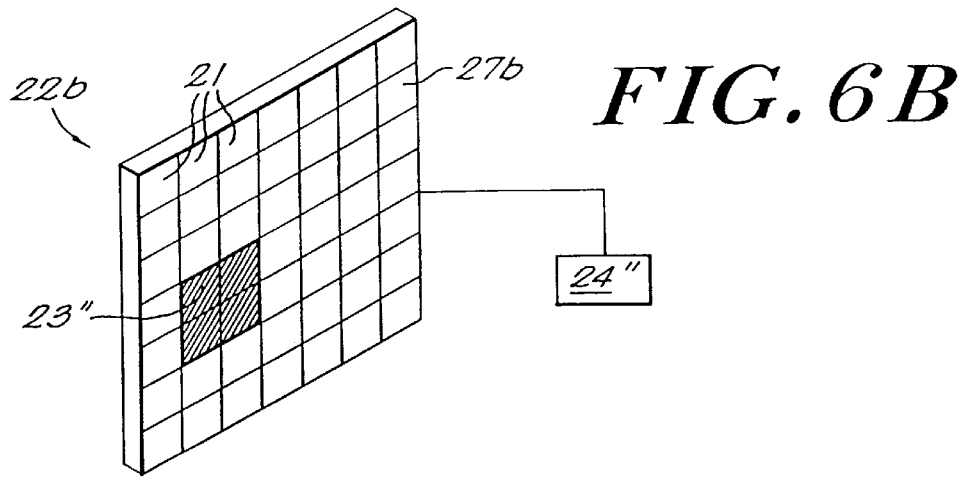
FIG. 6B shows the mask of FIGS. 1, and 3 implemented using a spatial light modulator.

In an alternative embodiment, shown in FIG. 6B, a mask 22b for use with the refractometer 10 of FIG. 1 is implemented by providing a spatial light modulator 27b having a multiplicity of light-modulating elements 21, each of which is operable in an "ON" state and in an "OFF" state. In the preferred embodiment, "ON" and "OFF" refer to the presence and absence of light respectively. However, "ON" and "OFF" can also refer to the presence and absence of any physically measurable parameter such as color, phase, or polarization state. Light-modulating elements in the "ON" state form an aperture 23" whose size, shape, and location on the mask are controllable by the distribution of light-modulating elements forming it. If these light-modulating elements 21 are liquid crystal elements, the ON and OFF states correspond respectively to the transmissive and opaque states of the liquid crystal element. When a liquid crystal element is in the ON state, light travels through that liquid crystal element toward the measurement plane 46 (FIG. 1). When a liquid crystal element is in its OFF state, light incident on that liquid crystal element is blocked and does not reach the measurement plane 46. Alternatively, if the light-modulating elements 21 are moveable micro-mirrors, the ON state corresponds to the position in which the micro-mirror reflects light toward the measurement plane 46 and the OFF state corresponds to the position in which the micro-mirror deflects light away from measurement plane 46. It will be appreciated by those skilled in the art that it is possible to use other types of spatial light modulators. In this alternative embodiment, the aperture controller 24" is a video display controller such as a VGA card of the type used to control the display of a typical general purpose digital computer.

By implementing the mask 22b with a spatial light modulator 27b (FIG. 6B) having individually addressable light-modulating elements 21, the invention enables apertures 23" of different sizes and shapes to be easily formed. For example, the spatial light modulator 27b has the ability to form annular apertures of varying inner and outer radii. Moreover, a mask 22b implemented by a spatial light modulator 27b is not subject to mechanical vibration and inertia, as is the mask 22a translated by a stepping motor M as shown in FIG. 6A.

The refractometer 10 shown in FIGS. 1 and 3 also includes an illumination pattern source 32 coplanar with an object plane 35. The object plane 35 is optically conjugate with the detector plane 47 and disposed along the optical axis X. An illumination controller 36, which is typically a video display board or VGA card of the type used to control a computer display, is connected to the illumination pattern source 32 to provide control of the pattern of illumination generated by the illumination source 38 (FIG. 3). A third lens 34 directs light from the illumination source 38 toward the mask 22. The illumination controller 36 is typically under control of the patient who manually selects the location of the illumination source 38 within the object plane 35 using a control device such as a joystick 52 in communication with the illumination controller 36. The control device 52 can also be a trackball, a mouse, a touch screen, or similar device. The illumination controller 36, the third lens 34, and the illumination pattern source 32 form a measurement optical subsystem 30.

Figure 7A:
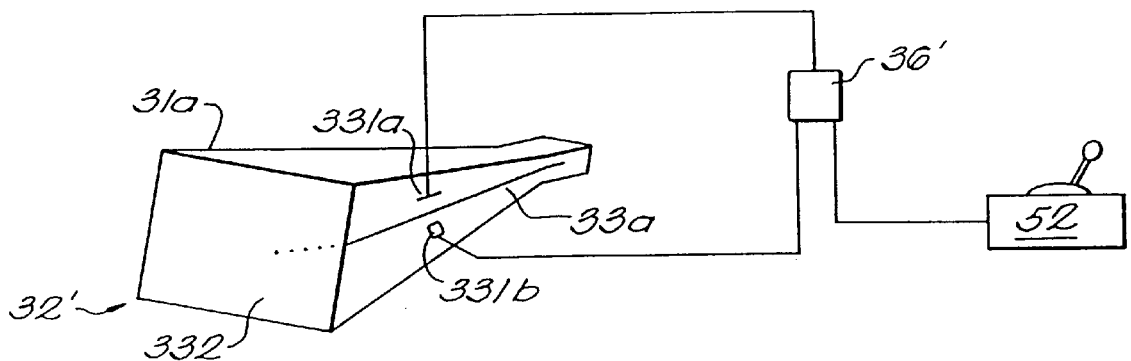
FIG. 7A shows an implementation of the illumination pattern source for the embodiments of FIGS. 1, 3, 4 and 5 as a cathode ray tube.
Figure 7B:
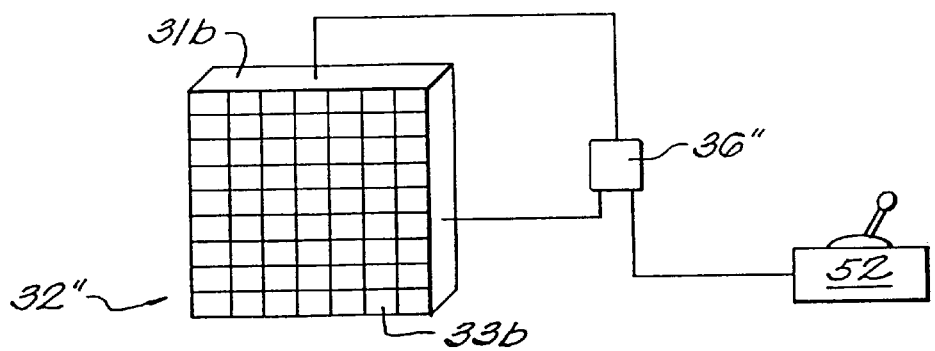
FIG. 7B shows an implementation of the illumination pattern source for the embodiments of FIGS. 1, 3, 4 and 5 as an array of light-emitting elements.
Figure 7C:
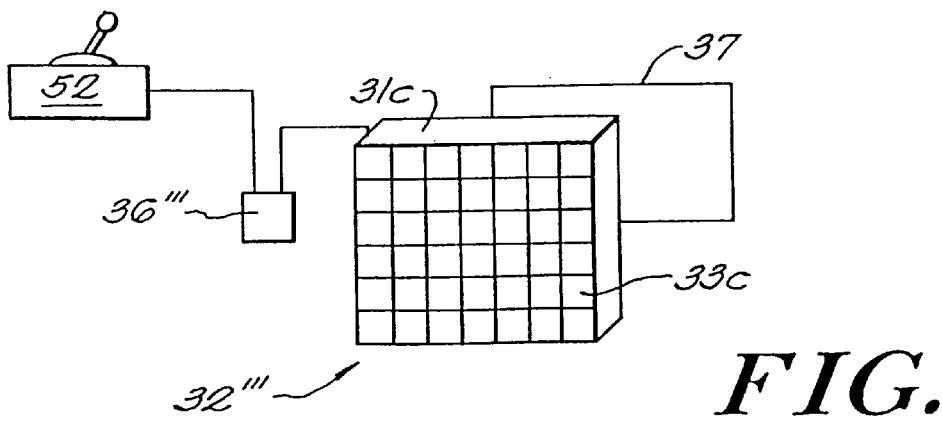
FIG. 7C shows an implementation of the illumination pattern source for the embodiments of FIGS. 1, 3, 4 and 5 as an array of light-modulating elements.

The illumination pattern source 32 of the refractometer 10 shown in FIG. 1 can be implemented using the illumination pattern sources 32', 32", 32''' of FIGS. 7A, 7B and 7C respectively.

In one embodiment, an illumination pattern source 32' is implemented, as shown in FIG. 7A, with a cathode ray tube 31a in which the deflection of the electron beam 33a is under the control of an illumination controller 36'. In an alternative embodiment, an illumination pattern source 32", as shown in FIG. 7B, employs an array 31b of individually addressable light emitting elements 33b, such as light emitting diodes, to selectively form apertures of different sizes and shapes. In this embodiment of the illumination pattern source 32, an illumination controller 36" controls which light emitting elements 33b are turned on. In yet another embodiment, as shown in FIG. 7C, the illumination pattern source 32''' includes a uniform light source 37 distal to the distal retinal conjugate plane 35 and an array 31c of individually addressable light-modulating elements 33c at the distal retinal conjugate plane 35. In this case, an illumination controller 36''' controls which light-modulating elements 33c block light generated by the uniform light source 37.

In all three illustrated embodiments of the illumination pattern source 32', 32", 32''', the illumination controller 36', 36", 36''' is typically a video display board or VGA card of the type used to control a computer display. The illumination controller 36', 36", 36''' receives from the joystick 52 a signal representative of the desired location of the illumination source 38 (FIG. 3) on the object plane 35. In the embodiment shown in FIG. 7A, the illumination controller 36' translates this signal into voltages which, when applied to orthogonal conducting plates 331a, 331b proximate to the electron beam 33a, deflect the electron beam 33a toward the desired location on the phosphorescent surface 332 of the cathode ray tube 31a. In the embodiment shown in FIG. 7B, the illumination controller 36" translates this signal into the addresses of the light emitting elements 33b at the desired location and sends a signal to those light emitting elements 33b to turn them on and off. In the embodiment shown in FIG. 7C, the illumination controller 36''' translates this signal into the addresses of the light modulating elements 33c at the desired location and sends a signal to those light-modulating elements 33c to turn them on and off, thereby spatially modulating light from the uniform light source 37.

Both the illumination controller 36 and the aperture controller 24 are connected to a processor 50 which determines the normal vector to the optimal wavefront associated with each point on the cornea 41 on the measurement plane 46 in a conventional manner.

Referring to FIG. 1, light emitted by the illuminated reticle 14 at the proximal retinal conjugate plane 15 illuminates a lens 16. The lens 16 focuses that light onto a reference pattern position 42 on the retina 43. This enables the patient to see a focused image of the reference mark 14b shown in FIG. 2.

Concurrently with the operation shown in FIG. 1, the aperture controller 24 moves the movable aperture 23 on the mask 22 to a designated location in the site-selection plane 25, as shown in FIG. 3. The illustrated refractometer 10 achieves this by either mechanically translating the mask 22 (see FIG. 6A) or, in the case of a mask implemented by a spatial light modulator, by addressing selected light-modulating elements (see FIG. 6B). Movement of the aperture 23 across the site-selection plane 25 has the effect of choosing a measurement site 40 on the measurement plane 46. When the cornea 41 of the patient's eye 45 is located approximately coplanar with the measurement plane 46, as described above, this has the effect of choosing a measurement site 40 on the cornea 41.

Using the joystick 52 connected to the illumination controller 36, the patient controls the position of the illumination source 38 on the illumination pattern source 32 (FIG. 3). Light generated at the object plane 35 by the illumination source 38 crosses the site-selection plane 25 by passing through the aperture 23 in the mask 22. This light is then directed toward the selected measurement site 40 on the measurement plane 46 that corresponds to the location of the moveable aperture 23 in the site-selection plane 25. As is apparent from inspection of FIG. 3, light passing through the moveable aperture 23 crosses the measurement plane 46 at the selected measurement site 40 independently of the position of the illumination source 38 on the object plane 35.

In a perfect eye, light crossing the measurement plane 46 comes to a focus at a measurement pattern position coincident with the reference pattern position 42. In an imperfect eye, that light is transmitted to a measurement pattern position 44 displaced from the reference pattern position 42. The measurement pattern position 44 depends on the local properties of the selected measurement site 40 and on the angle of incidence of the incoming light ray. The angle of incidence of the incoming light ray, in turn, depends on the location of the illumination source 38 on the object plane 35, a location which, as noted above, the patient controls by manipulating the joystick 52. Consequently, the patient has the ability to change the location of the measurement pattern position 44 on the retina 43 by manipulating the joystick 52 to change the location of the illumination source 38 on the object plane 35.

What the patient sees when the refractometer 10 is in use is therefore a stationary image of the reference mark 14b at the reference pattern position 42 together with a moveable image of the illumination source 38 at the measurement pattern position 44. The location of the reference pattern position 42 is controlled by the processor 50 through the aperture controller 24; the location of the measurement pattern position 44 is controlled by the patient through the joystick 52 and the illumination controller 36.

To obtain a measure of the normal vector of the optimal wavefront associated with a selected measurement site 40, the aperture controller 24, under the control of the processor 50, moves the aperture 23 to a location which corresponds to the location of the selected measurement site 40. The patient then moves the location of the illumination source 38 with a joystick 52 or similar device connected to the illumination controller 36, until the image of the illumination source on the measurement pattern position 44 (FIG. 3) coincides with the image of the reference pattern 14b (FIG. 2) on the reference pattern position 42 (FIG. 1).

By tracking the distance and the direction in which the patient moves the measurement pattern position 44 (FIG. 3), the processor 50 determines the normal vector of the optimal wavefront associated with the selected measurement site 40 on the patient's eye 45. The processor 50, which is also in communication with the illumination controller 36, determines the magnitude and the direction that the illumination source 38 had to be moved in order to align the measurement pattern position 44 with the image of the reference mark 14b at the reference pattern position 42 (FIG. 1). Using this information, the processor 50 calculates, using conventional means, the normal vector of the optimal wavefront associated with the selected measurement site 40 (FIG. 3) as well as a Seidel or polynomial expansion describing the optical system.

One skilled in the art will appreciate that the foregoing apparatus and method for measuring the normal vector to the optimal wavefront at a selected measurement site on the cornea 41 has the capacity for measurement of the normal vector to the optimal wavefront at a selected measurement site on a non-living optical system. This capacity for the measurement of the normal vector to the optimal wavefront in a non-living system with a refractometer according to the invention is exercised by replacing the retina 43 (FIG. 3) with a detector 43a (FIG. 8) having a light sensing array, such as a CCD camera or a quadrant detector, and by placing the pupil of the optical system 41a at the measurement plane 46. Such an embodiment is shown in the refractometer 10' of FIGS. 8 and 9.

Figure 8:
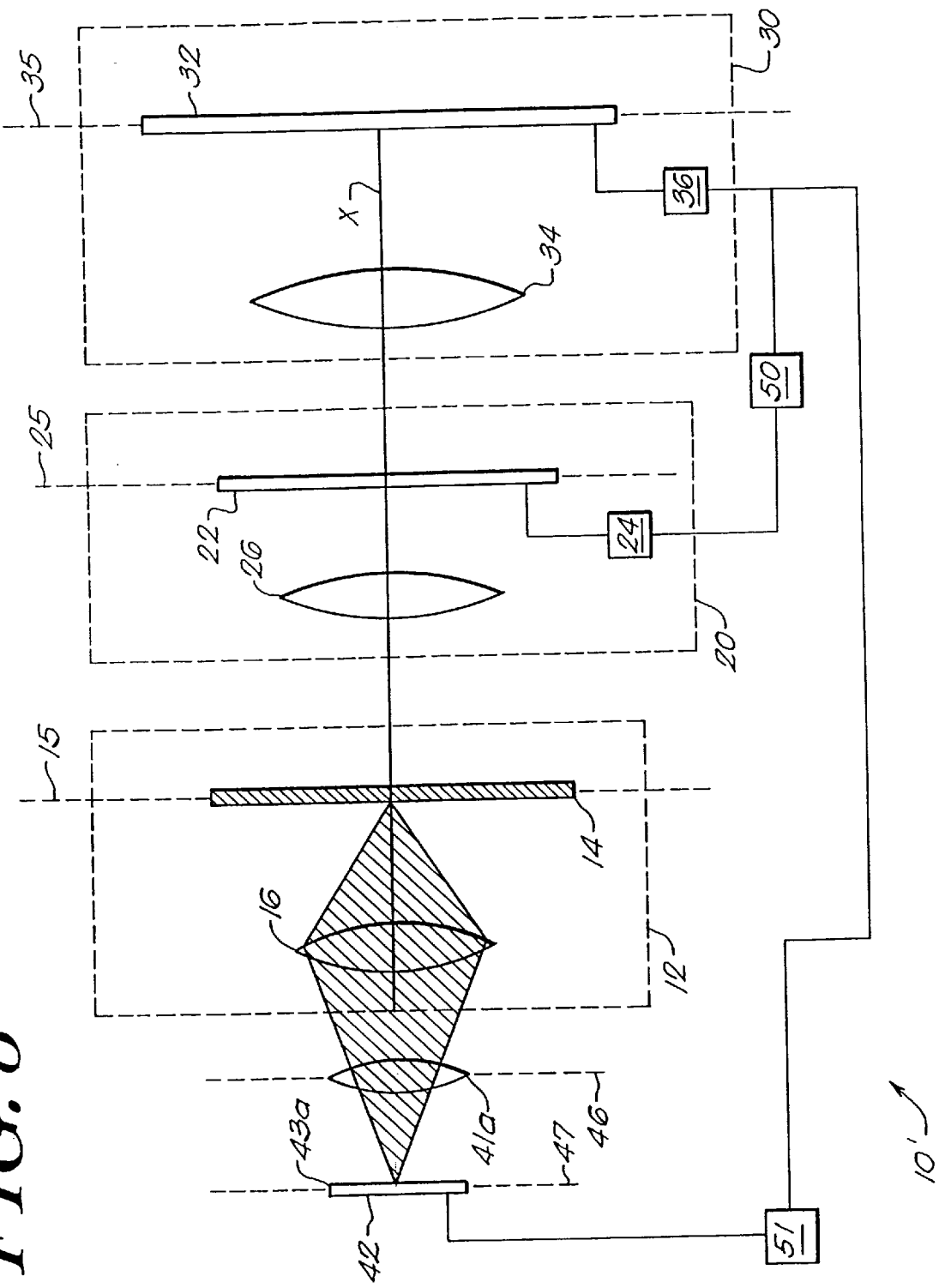
FIGS. 8–9 correspond to the embodiment illustrated in FIGS. 1 and 3 but with the eye replaced by a lens system and with the retina of the eye replaced by a detector.
Figure 9:
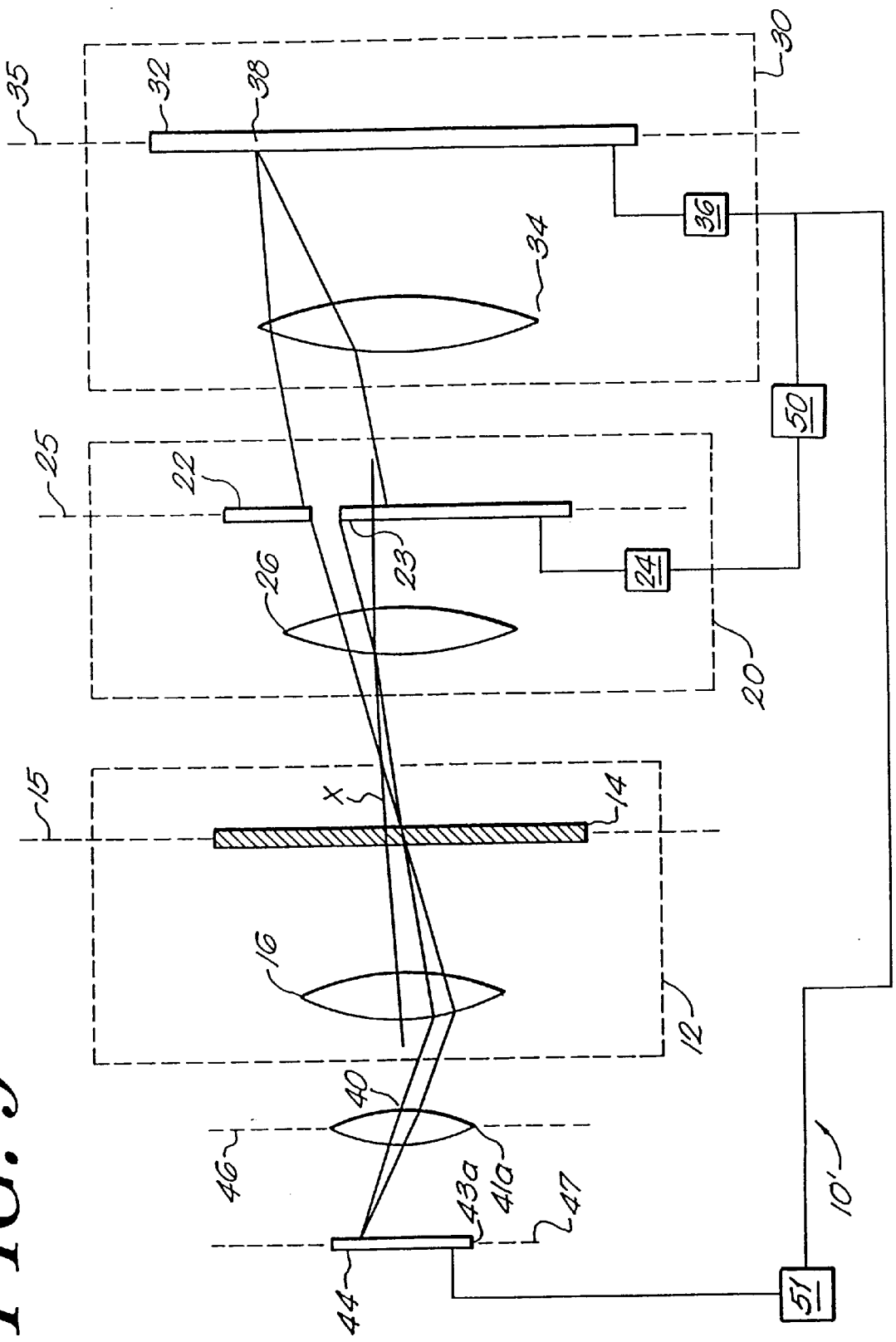

FIGS. 8 and 9 correspond to FIGS. 1 and 3 with the cornea 41 replaced by an optical system 41a whose optimal wavefront is sought and with the retina 43 replaced by a detector 43a which is responsive to the spatial location of an incident light source. The detector 43a is in communication with an alignment processor 51 which, based on the difference between the location of the reference pattern position 42 and the location of the measurement pattern position 44, signals the illumination controller 36 to move the illumination source 38 to align the measurement pattern position 44 with the reference pattern position 42. In this practice of the invention, the alignment processor 51 in effect replaces the function of the patient manipulating the joystick 52 (FIG. 3).

The alignment processor 51 (FIG. 9) is typically a general purpose digital computer implementing an algorithm for mimicking the function of a human patient manipulating a joystick 52 (FIG. 3) by executing an algorithm which results in the alignment of the measurement pattern position 44 with the reference pattern position 42. Such an algorithm accepts two inputs: the coordinates of the measurement pattern position 44 from the detector 43a and the coordinates of the reference pattern position 42 from the processor 50.

Using the coordinates of the measurement pattern position 44 and the reference pattern position 42, the alignment processor 51 instructs the aperture controller 24 to form an aperture 23 (see FIG. 9) which results in movement of the measurement pattern location 44 to reduce the difference between the measurement pattern location 44 and the reference pattern location 42. The algorithm executed by the alignment processor 51 is chosen from various commonly used optimization algorithms for minimizing the distance between two points by successive approximation, for example, the simplex algorithm, the method of steepest descent, or other such algorithms known in the art.

Figure 4:
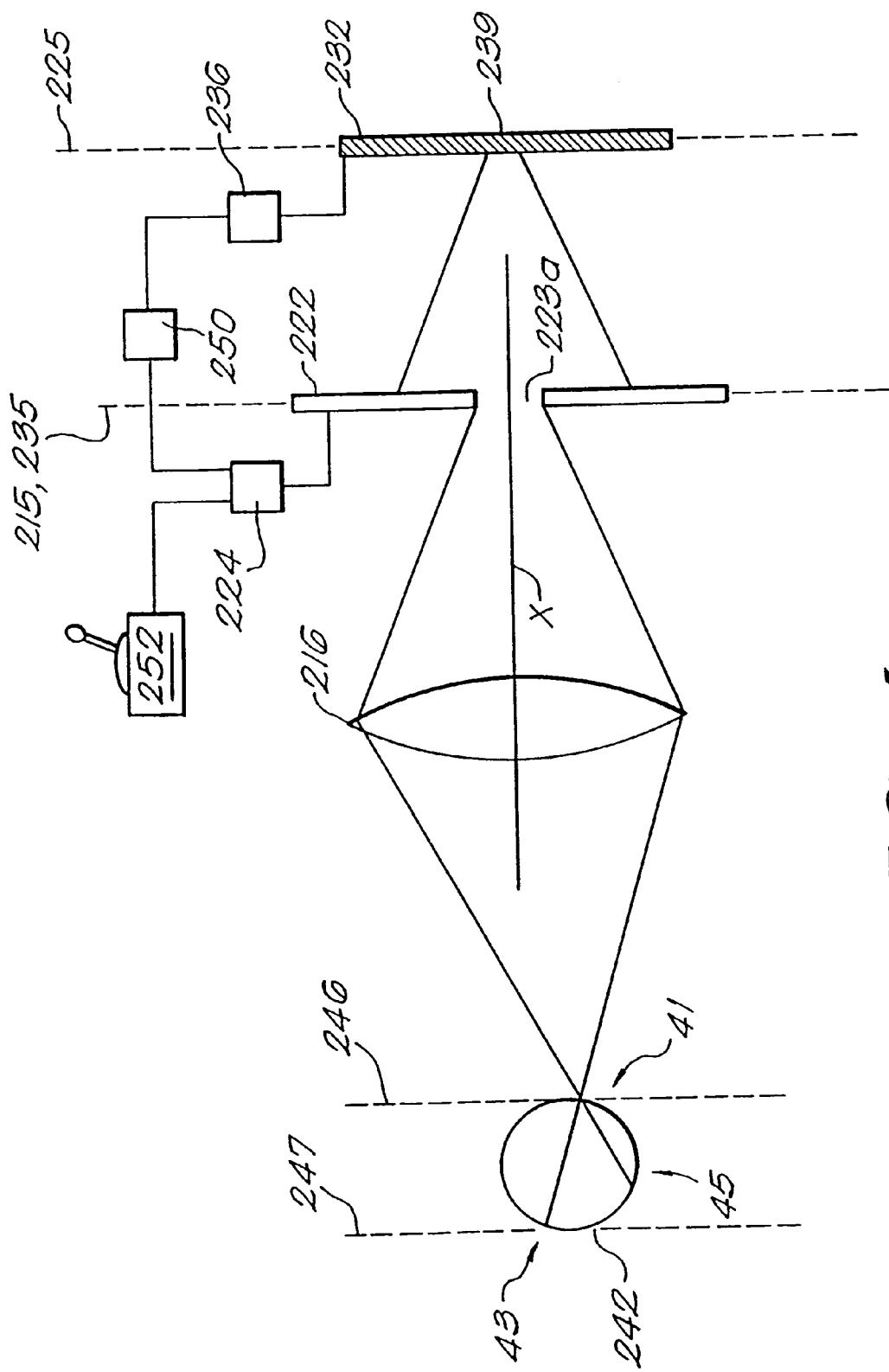
FIG. 4 shows a reference pattern being projected on the retina of an eye in a second embodiment of the invention.
Figure 5:
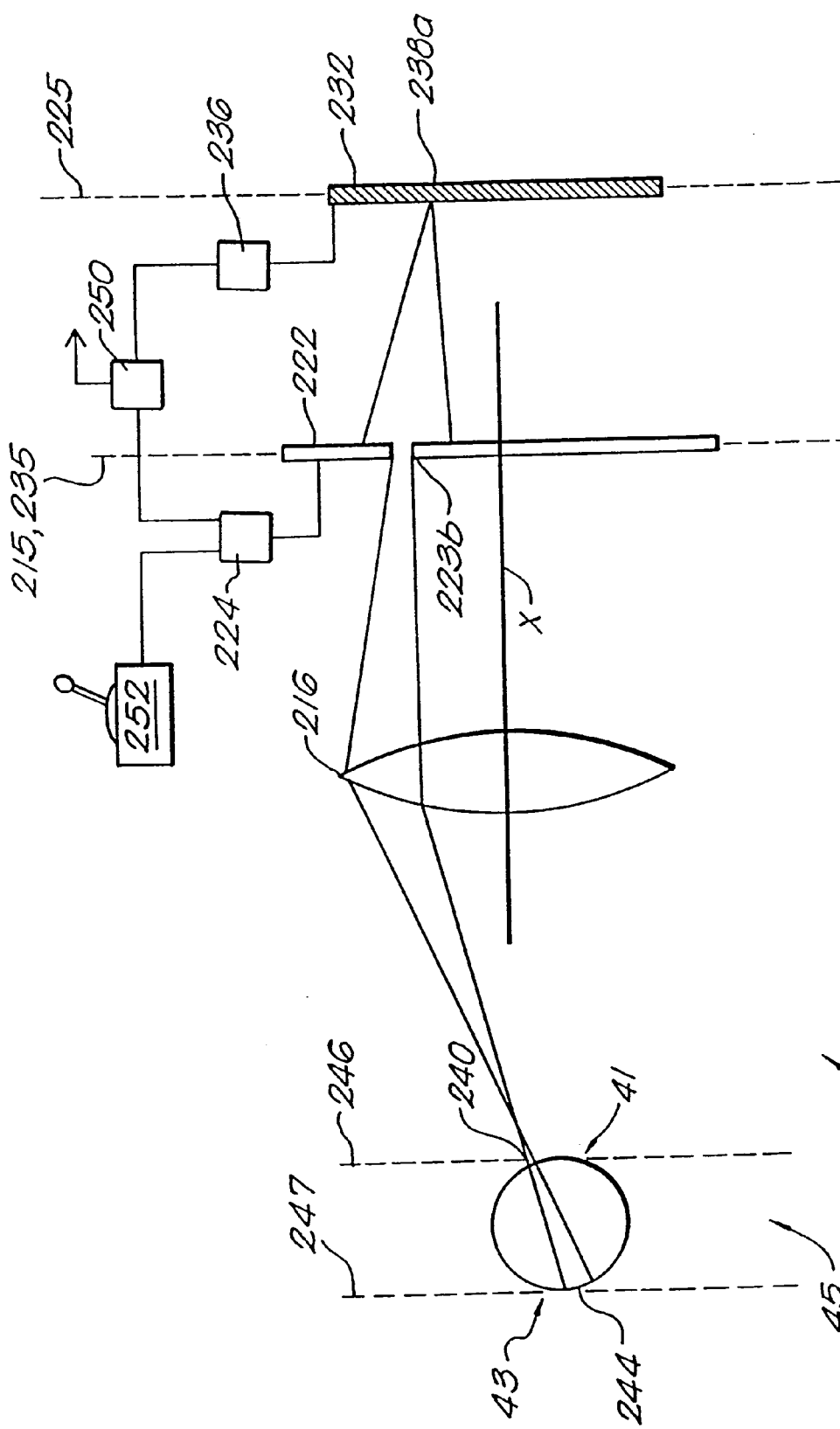
FIG. 5 shows a measurement pattern being projected on the retina of the eye in the embodiment depicted in FIG. 4.

In a second embodiment, shown operating in a reference mode in FIG. 4 and in a measurement mode in FIG. 5, a refractometer 11 incorporating the invention includes an illumination pattern source 232 which is coplanar with a site-selection plane 225. An illumination controller 236, which is typically a video display board or VGA card of the type used to control a computer display, is connected to the illumination pattern source 232 and provides control of the pattern of illumination generated by it. Elements of the refractometer 11 corresponding to elements of the refractometer 10 shown in FIG. 1 bear either the same reference numeral as that used in FIG. 1 or the same reference numeral but preceded by the numeral "2".

As shown in FIGS. 4 and 5, the second embodiment, like the first embodiment of FIGS. 1 and 3, includes a mask 222 disposed between a measurement plane 246 and the site-selection plane 225. The mask 222 has a moveable measurement aperture 223a (FIG. 4), 223b (FIG. 5) whose location is controlled by an aperture controller 224 which is typically a video display board or VGA card of the type used to control a computer display. However, unlike the mask in the first embodiment, this mask 222 is coplanar not with a site-selection plane 225 but with both the object plane 235 and a reference plane 215. As indicated in FIGS. 4 and 5, the reference plane 215 and the object plane in this second embodiment 11 are coplanar. This is unlike the first embodiment 10 in which the reference plane 15 and the object plane 35 are spatially separated (see FIGS. 1 and 3). Like this first embodiment 10 however, the reference plane 215 and the object plane 235 of the second embodiment are optically conjugate to a detector plane 247 and the site selection plane 225 is optically conjugate to the measurement plane 246.

When the refractometer 11 measures the optical properties of an eye 45, as shown in FIGS. 4 and 5, the eye 45 is positioned between the measurement plane 246 and the detector plane 247, with the retina 43 of the eye 45 being approximately coplanar with the detector plane 247 and with the cornea 41 being approximately coplanar with the measurement pane 246.

The refractometer 11 further includes a lens 216 disposed between the measurement plane 246 and the mask 222 for focusing light passing through the mask 222 at the measurement plane 246. Like the refractometer 10 of FIG. 1, the refractometer 11 of FIGS. 4 and 5 includes a processor 250 which is in communication with both the aperture controller 224 and the illumination controller 236. A joystick 252 or similar device provides an interface between a patient and the aperture controller 224 and thereby enables the patient to control the location of the movable aperture 223b during the measurement mode of operation shown in FIG. 5.

Figure 6C:
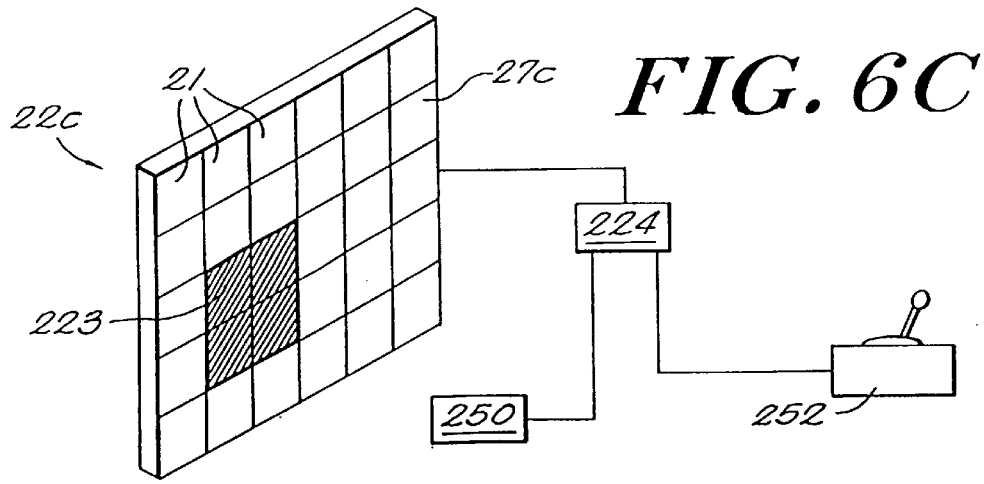
FIG. 6C shows the mask of FIGS. 4 and 5 implemented using a spatial light modulator.

FIG. 6C shows a mask 22c that is one preferred embodiment of the mask 222 for the refractometer 11 of FIGS. 4 and 5. The mask 22c is implemented by providing a spatial light modulator 27c having a multiplicity of light-modulating elements 21, each of which is operable in an "ON" state and in an "OFF" state. Light modulating elements in the "ON" state form an aperture 223 whose size, shape, and location on the mask 22c are controlled by the distribution of light-modulating elements forming it in the same manner as the mask 22b shown in FIG. 6B. In this alternative embodiment, the aperture controller 224 is a video display controller or VGA card of the type used to control the display of a typical general purpose digital computer. During the reference interval, the aperture controller 224 obtains the desired location of the aperture 223 from the processor 250. During the measurement interval, the aperture controller 224 obtains the desired location of the aperture 223 from the joystick 252 manipulated by the patient. The aperture controller 224 switches back and forth between these two modes of operation rapidly enough to cause a human observer to perceive the aperture selected by the processor 250 and the aperture selected by the joystick 252 as if they were on the mask 22c concurrently.

In operation, the refractometer 11 switches between operating in a reference mode, shown in FIG. 4, and operating in a measurement mode, shown in FIG. 5. During operation in the reference mode (FIG. 4), the refractometer 11 projects a reference pattern on a reference pattern position 242 on the eye. During operation in the measurement mode (FIG. 5), the refractometer 11 projects a measurement pattern selected on a measurement site 240 on the eye. The refractometer 11 alternates between operating in the measurement mode and operating in the reference mode rapidly enough so that, as a result of persistence of vision, the patient perceives the reference pattern and the measurement pattern as being concurrent.

When the refractometer 11 operates in the FIG. 4 reference mode, the aperture controller 224, under the control of the processor 250, forms a reference aperture 223a in the shape of a reference pattern. Concurrently, the illumination controller 236, also under the control of the processor 250, generates a reference illumination pattern 239. Light from the reference illumination pattern 239 passes through the reference aperture 223a and, as a result of the location of the reference aperture 223a on the reference plane 215, which, as pointed out above, is coplanar with the object plane 235, forms an image of the reference aperture 223a on a reference pattern position 242 on the detector plane 247. As a result, the patient perceives a reference pattern during the period in which the refractometer 11 operates in the reference mode.

It is possible to form the reference illumination pattern 239 by activating a broad area on the illumination pattern source 232 as shown in FIG. 4. When the reference illumination pattern is thus formed, the patient perceives a bright image of the reference aperture 223a. However, when this is the case, optical aberration introduced by the breadth of the reference illumination pattern 239 distorts the reference pattern . Alternatively, it is possible to form the reference illumination pattern 239 by activating a small area (not shown) on the illumination pattern source 232, in which case the patient perceives a dim but sharp image of the reference aperture 223a.

When the refractometer 11 operates in the FIG. 5 measurement mode, the aperture controller 224 forms a moveable measurement aperture 223b on the mask 222 in the object plane 235. The patient controls the location of this measurement aperture 223b by manipulating the joystick 252. Concurrently, the illumination controller 236 generates a measurement pattern 238a on the illumination pattern source 232.

Light from the measurement pattern 238a passes through the measurement aperture 223b. Since this light originates on the site-selection plane 225, it forms an image on the measurement plane 246 on which is disposed the cornea 41 of the patient's eye. Note that in this configuration, any light which leaks through the mask 222 originates on the object plane 235. Since this plane is conjugate to the retina, this leakage light forms a background image of the object plane 235 on the retina 43 rather than on the cornea 41. As a result, such leakage light does not enlarge the selected measurement site 240 on the cornea. This is a particularly useful property since, because of it, the light-modulating elements 21 in the spatial light modulators 27c used for implementing the mask 22c shown in FIG. 6C need not be perfectly opaque when operated in their "OFF" state.

With further reference to FIG. 5, light from the measurement pattern 238a illuminates the retina 43 at a measurement pattern position 244 determined by the measurement aperture 223b. As a result, the patient perceives an image of the measurement aperture 223b at a measurement pattern position 244 of the retina.

As the refractometer 11 switches between operating in reference mode, shown in FIG. 4, and operating in measurement mode, shown in FIG. 5, the patient sees a stationary image of the reference aperture at the reference pattern position 242 followed by a moveable image of the measurement aperture 223b at the measurement pattern position 244. As a result of persistence of vision, the patient perceives these images as being on the retina concurrently.

To determine the normal vector of the optimal wavefront at a selected measurement site 240 on the measurement plane 246 with the refractometer 11, the illumination controller 236, under the control of the processor 250, moves the measurement pattern 238a to a location which corresponds to the location of a selected measurement site 240. The patient then moves the location of the moveable measurement aperture 223b with a joystick 252 or similar device connected to the aperture controller 224 until the image of the measurement aperture 223b on the measurement pattern position 244 coincides with the image of the reference aperture 223a on the reference pattern position 242. By tracking the distance and the direction in which the patient moves the moveable measurement aperture 223b, the processor 250 evaluates the normal vector of the optimal wavefront associated with the selected measurement site 240 on the patient's eye.

Figure 10:
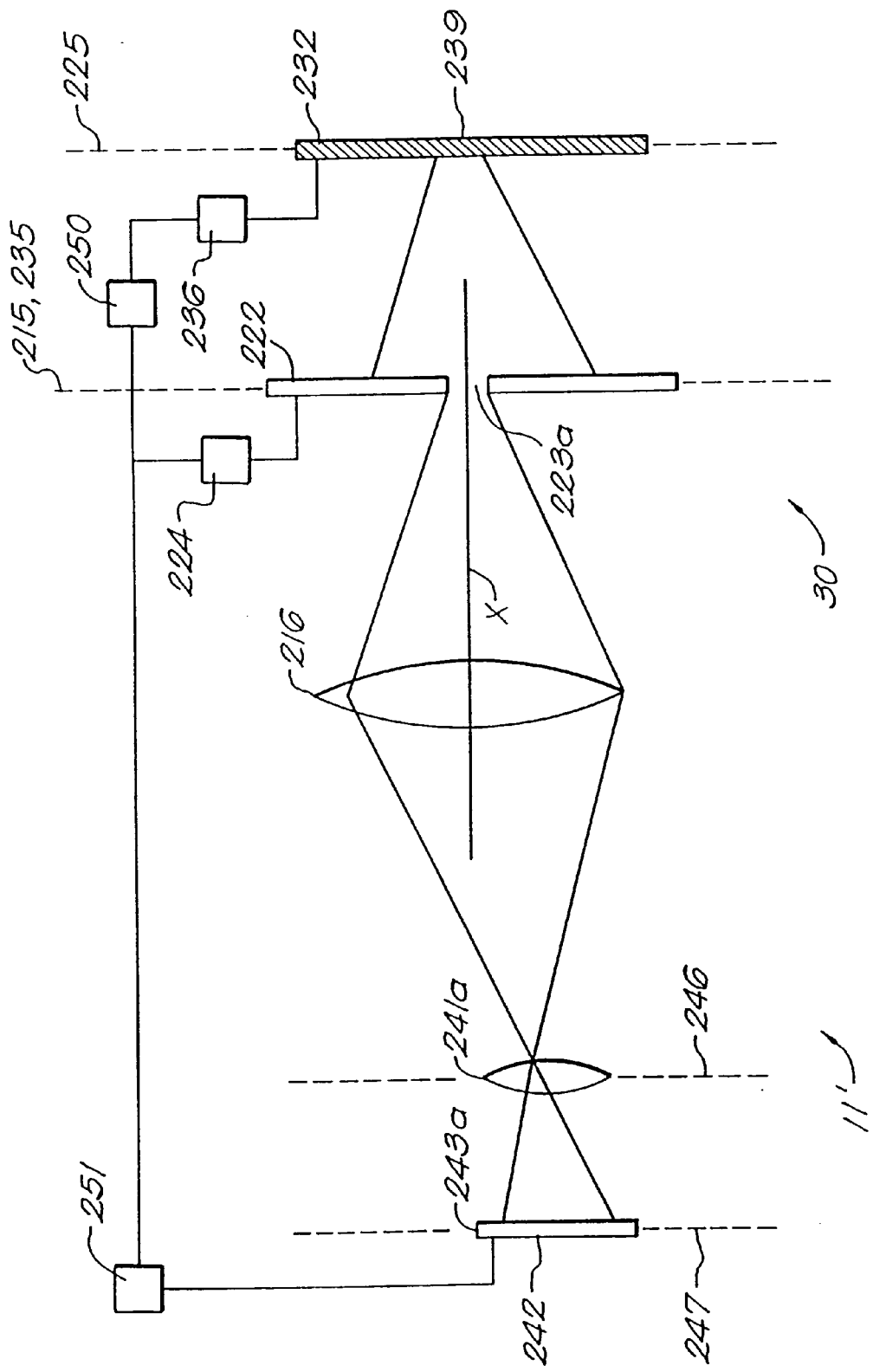
FIGS. 10–11 correspond to the embodiment illustrated in FIGS. 4 and 5 but with the eye replaced by a lens system and with the retina of the eye replaced by a detector.
Figure 11:
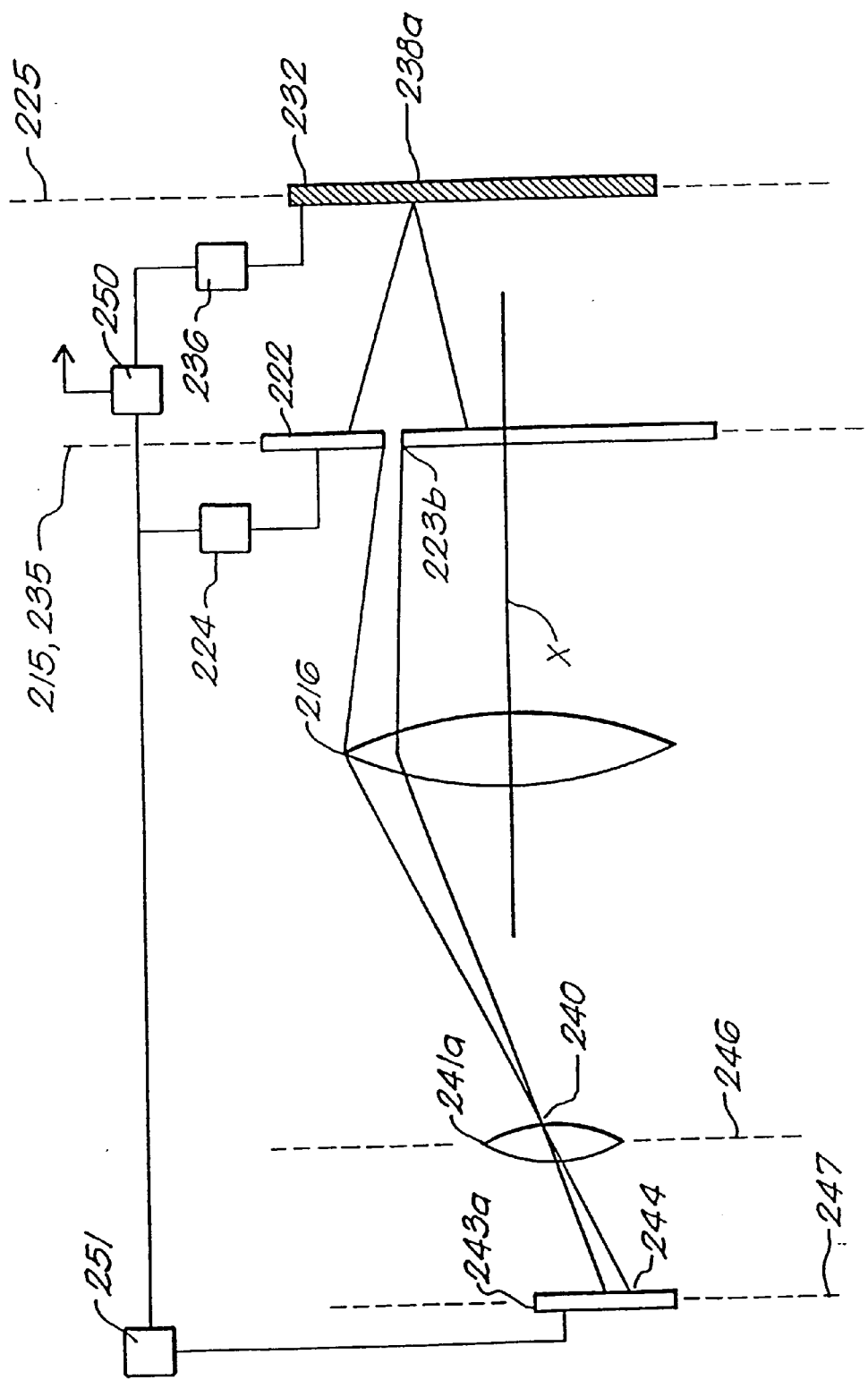
Figure 12A:
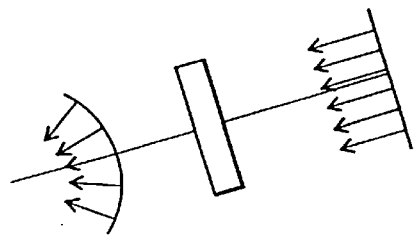
FIGS. 12A, 12B, and 12C, illustrate known physical principles underlying the invention, respectively: an ideal optical system which transforms a planar wavefront into a spherical wavefront, an optical system which transforms a planar wavefront into an irregular wavefront, and an optical system which transforms its optimal wavefront into a spherical wavefront.
Figure 12B:
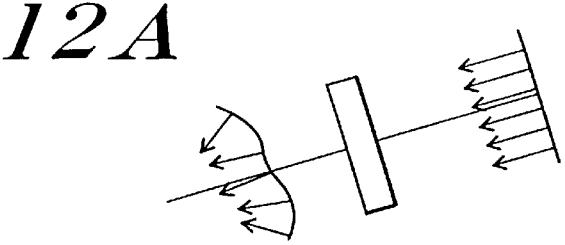
Figure 12C:
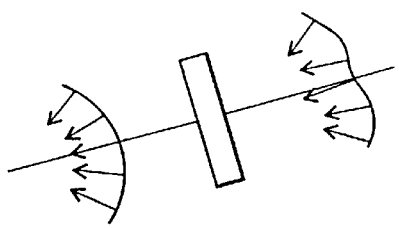

It will be appreciated by those skilled in the art that the refractometer 11 of this second embodiment can likewise be modified for determining the normal vector of the optimal wavefront associated with a lens or other inanimate refractive surface. For example, FIGS. 10 and 11 show a refractometer 11' similar to the refractometer 11 of FIGS. 4 and 5 in which the measurement plane 246 is coplanar with the pupil 241a of a lens system whose optimal wavefront is sought and in which the retina 43 is replaced by a detector 243a which is responsive to the spatial location of an incident light source. The detector 243a is in communication with an alignment processor 251 which, based on the difference between the location of the reference pattern position 242 and the location of the measurement pattern position 244, signals the aperture controller 224 to move the measurement aperture 223b so as to align the measurement pattern position 244 with the reference pattern position 242. In effect, the alignment processor 251 replaces the function of the patient manipulating the joystick 252 (FIG. 5).

The alignment processor 251 (FIG. 11) is typically a general purpose digital computer implementing a computer program for mimicking the function of a human patient manipulating a joystick 252 (FIG. 5) by aligning the measurement pattern position 244 with the reference pattern position 242 . Such a program accepts two inputs: the coordinates of the measurement pattern position 244 from the detector 243a and the coordinates of the reference pattern position 242 from the processor 250.

Using the coordinates of the measurement pattern position 244 and the reference pattern position 242, the alignment processor 251 instructs the aperture controller 224 to form an aperture 223 (see FIG. 11) which results in movement of the measurement pattern location 244 to reduce the difference between the measurement pattern location 244 and the reference pattern location 242. The computer program executed by the alignment processor 251 is chosen from various commonly used optimization algorithms for minimizing the distance between two points by successive approximation, for example, the simplex algorithm, the method of steepest descent, or other such algorithms known to those of skill in the art.

Figure 13:
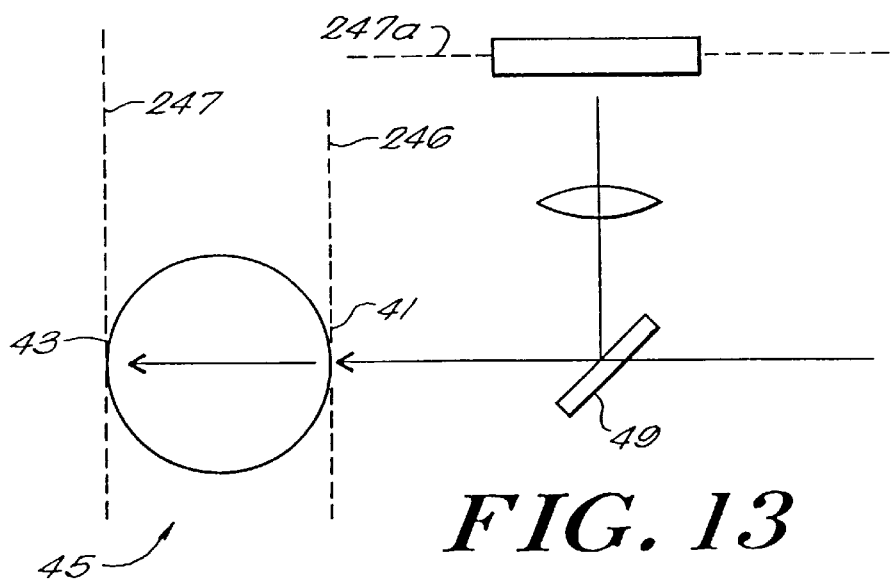
FIG. 13 shows a beamsplitter and lens adaptable for use with the embodiments of FIGS. 1, 3, 4, 5, 8, 9, 10 and 11 for transmitting the reference pattern and measurement pattern at the retina of an eye to a detector.

The addition of a beamsplitter 49 to any of the refractometers 10, 11, 10', 11', as shown in FIG. 13, enables the alignment processor 251, shown in FIGS. 10 and 11, to determine the optimal wavefront at the measurement plane 246 without the need to provide a detector 243a at the detector plane 247. This is accomplished by placing the detector 243a on a second detector plane 247a which is optically conjugate to the detector plane 247. The beamsplitter 49 is placed anywhere along the optical path between the measurement plane 246 and the site-selection plane 225. Preferably, the beamsplitter 49 is as close as possible to the measurement plane 46 to avoid incurring light loss by passing light re-emergent from the lens system through any other optical components between the measurement plane 46 and the site selection plane 25.

FIG. 13 shows an eye 45 having a cornea 41 approximately coplanar to the measurement plane 246 and a retina 43 approximately coplanar with the detector plane 247. As described below, the configuration shown in FIG. 13 enables the refractometer 11' to measure the optical properties of a patient's eye without the patient's active participation. This feature is especially useful when the patient lacks the fine motor skills necessary to manipulate the joystick 252 (FIG. 5) so as to align the measurement pattern position with the reference pattern position.

The beamsplitter 49 transmits a first portion of the light incident on it through the measurement plane 246 to the retina 43. Light re-emerging from the lens system, scattered or reflected from the retina or other structure 43, is, in part, reflected by the beamsplitter 49 to a detector 243a located on a plane conjugate to the retina. The detector 243a is in communication with a processor 251 as described above. Based on the difference between the location of the reference pattern position 242 and the location of the measurement pattern position 244, the processor 51 signals the aperture controller 224 to align the measurement pattern position 44 with the reference pattern position 242 by moving the measurement pattern aperture 223b. This feature is especially useful when a patient, such as a small child, cannot align the reference pattern position 42 with the measurement pattern position 44.

It will thus be seen that the invention efficiently attains the objects set forth above. Since certain changes may be made in the above constructions without departing from the scope of the invention, it is intended that all matter contained in the above description or shown in the accompanying drawings be interpreted as illustrative and not in a limiting sense.

It is also to be understood that the following claims are intended to cover all generic and specific features of the invention described herein, and all statements of the scope of the invention which as a matter of language might be said to fall there between. Having described the invention, what is claimed as new and secured by Letters Patent is:

What is claimed is:

1. A refractometer for determining the optimal wavefront at a measurement plane, said refractometer comprising a first spatial light pattern generator disposed at a first plane, said first plane being optically conjugate to said measurement plane, a second spatial light pattern generator coaxial with said first spatial light pattern generator, said second spatial light pattern generator disposed at a second plane optically conjugate to a detector plane, control means coupled to said first and second spatial light pattern generators for operating said refractometer in a measurement interval during which a measurement pattern is projected through a selected measurement site on said measurement plane and onto a measurement pattern position on said detector plane, and a reference interval during which a reference pattern is projected through a selected reference site on said measurement plane and onto a reference pattern position on said detector plane, and detector means in optical communication with said detector plane, said detector means providing an estimate of said measurement pattern position and said reference pattern position, automated alignment means in communication with said detector means for controlling an angle at which said measurement pattern is projected through said selected measurement site during said measurement interval, said angle being selected by said automatic alignment means on the basis of said estimate of said reference pattern position and said measurement pattern position.

2. The refractometer of claim 1 wherein said control means comprises means for operating said refractometer such that said measurement interval and said reference interval are successive intervals.

3. The refractometer of claim 1 wherein said control means comprises means for operating said refractometer such that said measurement interval is contemporaneous with said reference interval.

4. The refractometer of claim 1 further comprising reference target projection means coaxial with said first spatial light pattern generator for generating, on a plane optically conjugate to said detector plane, a reference pattern.

5. The refractometer of claim 4 wherein said reference target projection means comprises
a reference target disposed at a reference plane optically conjugate to said detector plane, and
a reference light source illuminating said reference target.

6. The refractometer of claim 5 wherein said reference plane is coplanar with said second plane.

7. The refractometer of claim 5 wherein said reference plane is disposed between said second plane and said detector plane.

8. The refractometer of claim 5 wherein said reference target comprises a reticle disposed at said reference plane.

9. The refractometer of claim 4 wherein said reference target projection means comprises
means forming an aperture in said second spatial light pattern generator,
illumination means for generating light passing through said aperture, and
means for coordinating the operation of said aperture forming means and said illumination means.

10. The refractometer of claim 9 wherein said means forming an aperture comprises means for selecting an extent of said aperture.

11. The refractometer of claim 1 further comprising site-selection means for selecting said measurement site.

12. The refractometer of claim 11 wherein said site-selection means comprises
means for forming a site-selection light source in said first plane, and
means for moving said site-selection light source to a selected point on said first plane.

13. The refractometer of claim 12 wherein said means for forming a moveable site-selection light source comprises
a cathode ray tube illuminated by a beam, said cathode ray tube disposed coplanar with said first plane, and
means for controlling the location of said beam on said cathode ray tube.

14. The refractometer of claim 12 wherein said means for forming a moveable site-selection light source comprises
an array of light-emitting elements disposed coplanar with said first plane, each of said light-emitting elements having an active state in which it emits light and a darkened state in which it does not emit light, and
means for selectively addressing said light-emitting elements.

15. The refractometer of claim 12 wherein said means for forming a site-selection light source in said first plane comprises means for selecting an extent of said site-selection light source.

16. The refractometer of claim 11 wherein said site-selection means comprises
means for forming a moveable site-selection aperture in said first plane, and
means for passing light through said site-selection aperture.

17. The refractometer of claim 16 wherein said means for forming a moveable site-selection aperture comprises
an opaque screen disposed coplanar with said first plane, said opaque screen having a site-selection aperture therethrough, and
means for moving said opaque screen, thereby moving said site-selection aperture in said first plane.

18. The refractometer of claim 16 wherein said means for forming a moveable site-selection aperture comprises
an array of light-modulating elements disposed coplanar with said first plane, each of said light modulating elements having an ON state and an OFF state, and
means for switching selected light-modulating elements from said array between said ON state and said OFF state, thereby forming a moveable site-selection aperture in said first plane.

19. The refractometer of claim 16 wherein said site-selection means further comprises means for selecting an extent of said aperture.

20. The refractometer of claim 1 wherein said alignment means comprises
a measurement light source moveable in said first plane, and
means for controlling the location of said light source within said first plane.

21. The refractometer of 20 wherein
said measurement light source comprises an array of light-modulating elements disposed coplanar with said first plane, each of said light modulating elements having an ON state and an OFF state, and
said location control means comprises means for switching selected light-modulating elements from said array between said ON state and said OFF state, thereby forming a moveable site-selection aperture in said first plane.

22. The refractometer of claim 20 wherein
said measurement light source comprises a cathode ray tube illuminated by a beam, said cathode ray tube disposed coplanar with said first plane, and
said location control means comprises means for controlling the location of said beam on said cathode ray tube.

23. The refractometer of claim 20 wherein said alignment means comprises
an array of light-emitting elements disposed coplanar with said first plane, each of said light-emitting elements having an active state in which it emits light and a darkened state in which it does not emit light, and
means for selectively addressing said light-emitting elements.

24. The refractometer of claim 1 wherein said control means further comprises means for repeating said reference interval and said measurement interval.

25. The refractometer of claim 1 wherein said detector means is disposed on a plane optically conjugate to said second plane to receive light from said site-selection plane, and said detector means is responsive to the spatial location of an incident light source.

26. The refractometer of claim 25 wherein said detector plane is coaxial with said measurement plane.

27. The refractometer of claim 25 wherein said automated alignment means further comprises means for receiving a signal from said detector means and means for responding to said signal by aligning said reference pattern position with said measurement pattern position.

28. The refractometer of claim 25 wherein said plane on which said detector is disposed is coplanar with said detector plane.

29. The refractometer of claim 25 wherein said detector means comprises a beamsplitter disposed between said second plane and said measurement plane to direct a first beam toward said detector plane and a second beam re-emegent from the lens system toward said detector.

30. The refractometer of claim 1 wherein said detector means comprises
   a spatially-responsive light-detector, and
   a beam splitter disposed to direct a portion of a beam reflected from a location on said detector plane toward a location on said spatially-responsive light-detector that corresponds to said location on said detector plane.

31. The refractometer of claim 1 wherein said automatic alignment means comprises
   a processor in communication with said detector means and configured to determine a vector along which to translate said measurement pattern position to coincide with said reference pattern position; and
   a controller in communication with said processor and said second spatial light pattern generator, said controller being configured to control said second spatial light pattern generator on the basis of instructions provided by said processor.

32. A refractometer for determining the optimal wavefront at a measurement plane, said refractometer comprising
   means for generating a spatially varying optical pattern, said optical pattern being disposed at a first plane optically conjugate to said measurement plane,
   means for modulating said spatially varying optical pattern, said modulating means being disposed coaxially with said pattern generating means on a second plane optically conjugate to a detector plane,
   control means coupled to said pattern generating means and said pattern modulating means for operating said refractometer in
      a measurement interval during which a measurement pattern is projected through a selected measurement site on said measurement plane and onto a measurement pattern position on said detector plane, and
      a reference interval during which a reference pattern is projected through a selected reference site on said measurement plane and onto a reference pattern position on said detector plane,
   detector means in optical communication with said detector plane, said detector means providing an estimate of said measurement pattern position and said reference pattern position,
   automatic alignment means in communication with said detector means for controlling an angle at which said measurement pattern is projected through said selected measurement site during said measurement interval, said angle being selected by said automatic alignment means on the basis of said reference pattern position and said measurement pattern position.

33. A method for determining the optimal wavefront at a measurement plane, said method comprising the steps of
   providing a first spatial light pattern generator disposed at a first plane, said first plane being optically conjugate to said measurement plane,
   providing a second spatial light pattern generator coaxial with said first spatial light pattern generator, said second spatial light pattern generator disposed at a second plane optically conjugate to a detector plane,
   projecting a measurement pattern through a selected measurement site on said measurement plane and onto a measurement pattern position on said detector plane during a measurement interval,
   projecting a reference pattern through a reference pattern site on said measurement plane and onto a reference pattern position on said detector plane during a reference interval,
   determining said measurement pattern position and said reference pattern position, and
   aligning said measurement pattern position with said reference pattern position on said detector plane.

34. The method of claim 33 wherein said step of projecting said measurement pattern follows said step of projecting said reference pattern.

35. The method of claim 33 wherein said step of projecting said measurement pattern and said step of projecting said reference pattern occur contemporaneously.

36. The method of claim 33 wherein said step of projecting a reference pattern further comprises the step of generating, on a plane optically conjugate to said detector plane, a reference pattern.

37. The method of claim 36 wherein said step of generating a reference pattern comprises the step of
   illuminating a reference target disposed at a reference plane optically conjugate to said detector plane.

38. The method of claim 37 further comprising the step of positioning said reference plane to be coplanar with said second plane.

39. The method of claim 37 further comprising the step of positioning said reference plane between said second plane and said detector plane.

40. The method of claim 36 wherein said step of projecting a reference pattern comprises the steps of
   forming an aperture in a second spatial light pattern generator disposed at a plane optically conjugate to said detector plane, and
   passing light through said aperture.

41. The method of claim 40 further comprising the step of selecting an extent of said aperture.

42. The method of claim 33 further comprising the step of selecting said measurement site.

43. The method of claim 42 wherein said step of selecting said measurement site comprises the steps of
   forming a site-selection light source in a first plane conjugate to said measurement plane, and
   moving said site-selection light source to a selected point on said first plane.

44. The method of claim 43 wherein said step of forming a moveable site-selection light source comprises the step of
   controlling the location of a beam on a cathode ray tube illuminated by said beam, said cathode ray tube disposed coplanar with said first plane.

45. The method of claim 43 wherein said step of forming a moveable site-selection light source comprises the step of
   selectively addressing said light-emitting elements from an array of light-emitting elements disposed coplanar with said first plane, each of said light-emitting elements having an active state in which it emits light and a darkened state in which it does not emit light.

46. The method of claim 43 wherein said step of forming a site-selection light source comprises the step of specifying an extent of said site-selection light source.

47. The method of claim 42 wherein said step of selecting said measurement site comprises the steps of forming a moveable site-selection aperture in said first plane, and passing light through said site-selection aperture.

48. The method of claim 47 wherein said step of forming a moveable site-selection aperture comprises the step of moving an opaque screen disposed coplanar with said first plane in a direction coplanar with said first plane, said opaque screen having a site-selection aperture therethrough.

49. The method of claim 47 wherein said step of forming a moveable site-selection aperture comprises the steps of providing an array of light-modulating elements disposed coplanar with said first plane, each of said light modulating elements having an ON state and an OFF state, and switching selected light-modulating elements from said array between said ON state and said OFF state, thereby forming a moveable site-selection aperture in said first plane.

50. The method of claim 47 wherein said step of forming a movable site-selection aperture comprises the step of specifying an extent of said site-selection aperture.

51. The method of claim 33 wherein said aligning step comprises the step of controlling the location of a measurement light source within said first plane.

52. The method of claim 51 wherein said controlling step comprises the steps of providing an array of light-modulating elements disposed coplanar with said first plane, each of said light modulating elements having an ON state and an OFF state, and switching selected light-modulating elements from said array between said ON state and said OFF state, thereby forming a moveable site-selection aperture in said first plane.

53. The method of claim 51 wherein said controlling step comprises the steps of providing a cathode ray tube illuminated by a beam, said cathode ray tube disposed coplanar with said first plane, and controlling the location of said beam on said cathode ray tube.

54. The method of claim 51 wherein said aligning step comprises the steps of providing an array of light-emitting elements disposed coplanar with said first plane, each of said light-emitting elements having an active state in which it emits light and a darkened state in which it does not emit light, and selectively addressing said light-emitting elements.

55. The method of claim 33 further comprising the step of detecting, at the detector plane, the spatial location of an incident light source.

56. The method of claim 55 wherein said detecting step includes the step of providing a CCD array.

57. The method of claim 55 wherein said detecting step includes the step of providing a quadrant detector.

58. The method of claim 33 wherein said estimating step comprises the steps of:

providing a spatially-responsive light-detector, and diverting a beam from said location on said detector plane to a corresponding location on said spatially-responsive light-detector.

59. The method of claim 33 wherein said aligning step comprises the steps of determining a vector along which to translate said measurement pattern position toward said reference pattern position, and controlling said measurement pattern position on the basis of said vector.

60. A refractometer for determining the normal vector to a wavefront at a selected measurement site on a cornea of a patient, said refractometer comprising reference projection means coaxial with an optical axis for projecting, onto a reference pattern position on a retina of a patient, a reference pattern, site-selection means, coaxial with said optical axis, for selecting said selected measurement site, measurement projection means, coaxial with said optical axis, for projecting a measurement pattern through said selected measurement site for refraction to a measurement pattern position on said retina, detector means in optical communication with said retina, said detector means providing an estimate of the locations of said measurement pattern position and said reference pattern position, and automated alignment means for changing the location of said measurement pattern position on the basis of said estimate, said alignment means permitting alignment of said measurement pattern position with said reference pattern position.

61. The refractometer of claim 60 wherein said detector means comprises a spatially-responsive light-detector, and a beamsplitter disposed to direct a portion of a beam reflected from a location on said retina toward a location on said spatially-responsive light-detector that corresponds to said location on said retina.

62. The refractometer of claim 60 wherein said automated alignment means comprises a processor in communication with said detector means and configured to determine a vector along which to translate said measurement pattern position to coincide with said reference pattern position, and a controller in communication with said processor and said site-selection means, said controller configured to control said site-selection means on the basis of instructions provided by said processor.

63. A refractometer for determining the optimal wavefront at a measurement plane, said refractometer comprising pattern generating means for generating a spatially varying optical pattern, said optical pattern being disposed at a first plane conjugate to a detector plane, pattern modulating means for modulating said spatially varying optical pattern, said pattern modulating means being disposed coaxially with said pattern generating means on a second plane optically conjugate to said measurement plane, control means coupled to said first and second spatial light pattern generators for operating said refractometer in a measurement interval during which a measurement pattern is projected through a selected measurement site on said measurement plane and onto a measurement pattern position on said detector plane, and a reference interval during which a reference pattern is projected through a selected reference site on said measurement plane and onto a reference pattern position on said detector plane, detector means in optical communication with said detector plane, said measurement means configured to provide an estimate of the locations of said reference pattern position and said measurement pattern position, and automated alignment means in communication with said measurement means for controlling, on the basis of said estimate, an angle at which said measurement pattern is projected through said selected measurement site during said measurement interval.

64. The refractometer of claim 63 wherein said detector means comprises a spatially-responsive light-detector, and a beamsplitter disposed to direct a portion of a beam reflected from a location on said detector plane toward a location on said spatially-responsive light-detector that corresponds to said location on said detector plane.

65. The refractometer of claim 63 wherein said detector means comprises a spatially-responsive light-detector, and a beamsplitter disposed to direct a portion of a beam reflected from a location on said detector plane toward a location on said spatially-responsive light-detector that corresponds to said location on said detector plane.

66. The refractometer of claim 63 wherein said automated alignment means comprises a processor in communication with said detector means and configured to determine a vector along which to translate said measurement pattern position toward said reference pattern position, and a controller in communication with said processor and said pattern modulating means, said controller being configured to control said pattern modulation means on the basis of instructions provided by said processor.

* * * * *

UNITED STATES PATENT AND TRADEMARK OFFICE
CERTIFICATE OF CORRECTION

PATENT NO.   : 6,099,125
DATED        : August 8, 2000
INVENTOR(S)  : Webb et al.

It is certified that error appears in the above-identified patent and that said Letters Patent is hereby corrected as shown below:

<u>Column 1,</u>
Line 3, the following two sentences should be inserted:
-- STATEMENT OF RIGHTS
This invention was made with government support under Grant DE-FG 02-91ER61229 awarded by the Department of Energy. The Government has certain rights in the invention. --

Signed and Sealed this

Seventh Day of October, 2003

JAMES E. ROGAN
*Director of the United States Patent and Trademark Office*